US005648493A

United States Patent [19]
Petersen et al.

[11] Patent Number: 5,648,493
[45] Date of Patent: Jul. 15, 1997

[54] PREPARATION OF 7-(3-AMINO- AND 3-AMINO-METHYL-1-PYRROLIDINYL)-3-QUINOLONECARBOXYLIC ACIDS AND -NAPHTHYRIDONECARBOXYLIC ACIDS

[75] Inventors: Uwe Petersen, Leverkusen; Andreas Krebs, Odenthal; Thomas Schenke, Bergisch-Gladbach; Klaus Grohe; Michael Schriewer, both of Odenthal; Ingo Haller, Wuppertal; Karl Georg Metzger, Wuppertal; Rainer Endermann, Wuppertal; Hans-Joachim Zeiler, Velbert, all of Germany

[73] Assignee: Bayer Aktiengesellschaft, Leverkusen, Germany

[21] Appl. No.: 717,748

[22] Filed: Jun. 19, 1991

Related U.S. Application Data

[62] Division of Ser. No. 529,016, May 25, 1990, Pat. No. 5,061,712.

[30] Foreign Application Priority Data

Jun. 7, 1989 [DE] Germany ............ 39 18 544.3

[51] Int. Cl.$^6$ ............ C07D 215/233; C07D 401/04
[52] U.S. Cl. ............ 546/156; 546/123; 546/146
[58] Field of Search ............ 546/146, 123, 546/156

[56] References Cited

U.S. PATENT DOCUMENTS

| | | | |
|---|---|---|---|
| 4,556,658 | 12/1985 | Grohe et al. | 514/254 |
| 4,666,920 | 5/1987 | Grohe et al. | 546/156 |
| 4,762,845 | 8/1988 | Chu et al. | 514/312 |
| 4,780,468 | 10/1988 | Bridges | 514/312 |
| 4,962,112 | 10/1990 | Rosen et al. | 546/156 |

FOREIGN PATENT DOCUMENTS

| | | |
|---|---|---|
| 0132845 | 2/1985 | European Pat. Off. |
| 0183129 | 6/1986 | European Pat. Off. |
| 0191451 | 8/1986 | European Pat. Off. |
| 0195316 | 9/1986 | European Pat. Off. |
| 0208210 | 1/1987 | European Pat. Off. |
| 0259804 | 3/1988 | European Pat. Off. |
| 2739313 | 3/1979 | Germany. |

OTHER PUBLICATIONS

H. Beyer, Textbook of Organic Chemistry (1978), p. 145.

Houben Weyl, Methods of Organic Chemistry, vol. XI/1, pp. 24–27, 1957.

Chemical Abstracts, vol. 105, No. 23, Abstract 208,850w, Dec. 8, 1986, p. 593.

Chemical Abstracts, vol. 107, No. 9, Abstract 77,777u, Aug. 31, 1987, p. 703.

*Primary Examiner*—C. Warren Ivy
*Assistant Examiner*—D. Margaret M. Mach
*Attorney, Agent, or Firm*—Sprung Horn Kramer & Woods

[57] ABSTRACT

Process for the preparation of antibacterial compounds of the formula $$\text{(I)}$$

comprises condensing an oxo compound of the formula $$\text{(V)}$$

with an amino compound of the formula $$\text{(VI)}$$

to produce a compound of the formula $$\text{(III)}$$

reacting the compound of the formula (III) with a compound of the formula $$\text{(II)}$$

to give a compound of the formula $$\text{(IV)}$$

and then eliminating the amino-protective group

3 Claims, No Drawings

PREPARATION OF 7-(3-AMINO- AND 3-AMINO-METHYL-1-PYRROLIDINYL)-3-QUINOLONECARBOXYLIC ACIDS AND -NAPHTHYRIDONECARBOXYLIC ACIDS

This is a division of application Ser. No. 529,016, filed May 25, 1990, now U.S. Pat. No. 5,061,712.

The present invention relates to a process for the preparation of 7-(3-amino- and 3-aminomethyl-1-pyrrolidinyl)-3-quinolonecarboxylic acids and -naphthyridonecarboxylic acids which have been disclosed as antibacterial agents and are prepared by reaction of 7-halogeno-3-quinolonecarboxylic acids or -naphthyridonecarboxylic acids with 3-aminopyrrolidine or 3-aminomethylpyrrolidine in free form or in the form of the 3-acylamino- or 3-acylaminomethyl-pyrrolidines and subsequent elimination of the acyl radicals. Reactions of this type have been described, for example, in the following patent applications: European Patent Applications 153,163, 183,129, 195,316, 198,678, 200,307, 207,497 and 236,673; U.S. Pat. No. 4,550,104; and Japanese Patent Application 63,166,876.

However, these processes have various disadvantages:

1. If 3-amino- or 3-aminomethylpyrrolidones in which the amino group is not protected by an acyl radical are employed, the reaction with 7-halogenoquinqlonecarboxylic acids does not proceed selectively in the desired sense by substitution on the pyrrolidine nitrogen, but the presence of the free amino group also leads to the occurrence of by-products which would have to be removed by expensive purification.

2. If 3-acylamino- or 3-acylaminomethylpyrrolidines in which acetyl or tert.-butoxycarbonyl is usually used as the acyl radical are employed, the reactions proceed selectively on the pyrrolidine nitrogen to give the 7-(3-acylamino- or 3-acylaminomethyl-1-pyrrolidinyl)-3-quinolonecarboxylic acids. To prepare the free 7-(3-amino- or 3-aminomethyl-1-pyrrolidinyl)-3-quinolonecarboxylic acids, subsequent elimination of the protective group by treatment with aqueous sodium hydroxide solution under the influence of heat or with hydrochloric acid or trifluoroacetic acid is required. This can again lead to undesirable side reactions: for example the highly active 8-bromo- or 8-chloro-3-quinolonecarboxylic acids can in some cases lose the halogen atom in the 8-position during deblocking with hydrochloric acid.

In order to avoid these disadvantages, it was necessary to develop a process which makes it possible to prepare 7-(3-amino-and 3-aminomethyl-1-pyrrolidinyl)-3quinolonecarboxylic acids in a high purity in a simple manner.

It has been found that the compounds of the formula (I), which can exist as enantiomeric or diastereomeric mixtures or in the enantiomerically or diastereomerically pure form

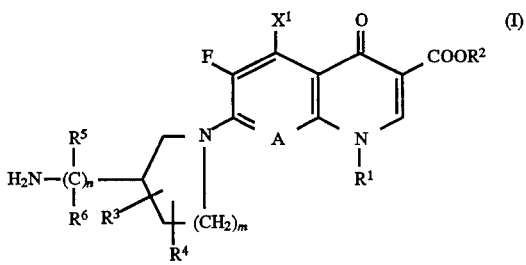

and in which $X^1$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or alkyl having 1 to 4 carbon atoms, $R^1$ represents straight-chain or branched alkyl having 1 to 5 carbon atoms, which can optionally be substitutes by 1 to 3 halogen atoms, or alkenyl having 2 to 4 carbon atoms, cycloalkyl having 3 to 6 carbon atoms, 2-hydroxyethyl, methoxy, amino, methylamino, ethylamino, dimethylamino or phenyl which is optionally substituted by 1 or 2 fluorine atoms, $R^2$ represents hydrogen, alkyl having 1 to 4 carbon atoms or (5-methyl-2-oxo-1,3-dioxol-4-yl)-methyl, $R^3$ represents hydrogen, $C_1$-$C_3$-alkyl, hydroxyl, $C_1$-$C_3$-alkoxy, $C_1$-$C_3$-alkylthio or halogen, $R^4$ represents hydrogen or methyl, $R^5$ and $R^6$ are identical or different and represent hydrogen or methyl, m represents 0, 1 or 2, n represents 0 or 1 and A represents N or C—$R^7$, wherein
$R^7$ represents H, halogen, methyl, cyano, nitro, hydroxyl or methoxy, or together with $R^1$ can also form a bridge having the structure

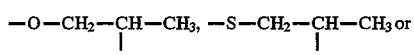

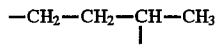

which can have the R— or S-configuration, are obtained by a process in which compounds of the formula (II)

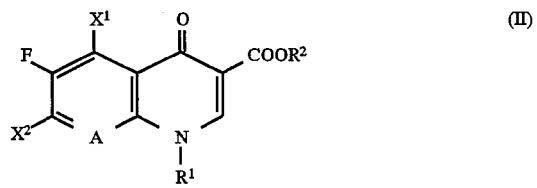

in which
$X^1$, $R^1$, $R^2$ and A have the abovementioned meaning and
$X^2$ represents halogen, are reacted with compounds of the formula (III)

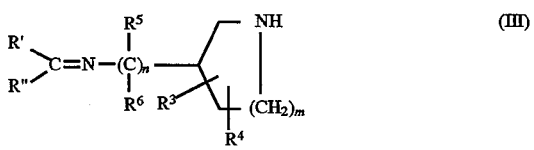

in which
$R^3$, $R^4$, $R^5$, $R^6$, m and n have the abovementioned meanings,

R' represents hydrogen, straight-chain or branched alkyl having 1 to 10 carbon atoms or phenyl, which can optionally be substituted by one to five identical or different substituents from the group comprising $C_1$-$C_4$-alkyl, $C_1$-$C_4$-alkoxy, $C_1$-$C_2$-alkylthio, hydroxyl, nitro, halogen, carboxyl, $C_1$-$C_4$-alkoxycarbonyl, cyano and phenyl, or represents naphthyl, and R" represents hydrogen, straight-chain or branched alkyl having 1 to 5 carbon atoms or phenyl, wherein R' and R", together with the carbon atom to which they are bonded, can also form a 5- or 6-membered aliphatic ring which is optionally substituted by one or more methyl or ethyl radicals, if appropriate in the presence of an acid-binding agent, to give compounds of the formula (IV)

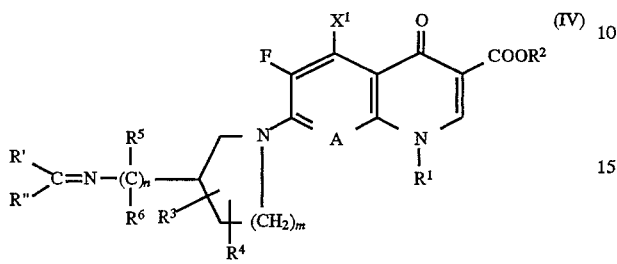

in which $X^1$, A, $R^1$, $R^2$, $R^3$, $R^4$, $R^5$, $R^6$, R', R", m and n have the abovementioned meanings, and the amino-protective group is then eliminated.

Compounds which are preferred for the process according to the invention are those of the formula (II)

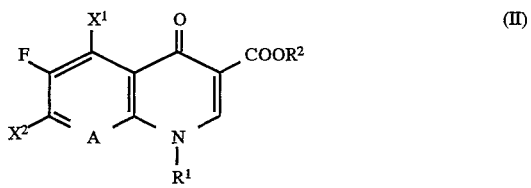

in which $X^1$ represents hydrogen, amino, hydroxyl, alkoxy having 1 or 2 carbon atoms, fluorine, chlorine, bromine or alkyl having 1 to 3 carbon atoms, $X^2$ represents fluorine or chlorine, $R^1$ represents straight-chain or branched alkyl having 1 to 4 carbon atoms, which can optionally be substituted by 1 to 3 fluorine atoms, or alkenyl having 2 to 3 carbon atoms, cycloalkyl having 3 or 4 carbon atoms, 2-hydroxyethyl, 2-fluoroethyl, methylamino, ethylamino, dimethylamino or phenyl which is optionally substituted by 1 or 2 fluorine atoms, $R^2$ represents hydrogen or alkyl having 1 to 3 carbon atoms and A represents N or C—$R^7$, wherein $R^7$ represents H, fluorine, chlorine, bromine, methyl, hydroxyl or methoxy, or together with $R^1$ can also form a bridge having the structure

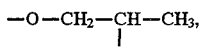

and those of the formula (III)

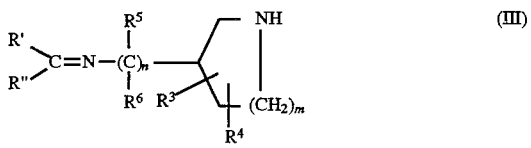

in which $R^3$ represents hydrogen, methyl, ethyl, hydroxyl, methoxy, ethoxy, methylthio, ethylthio, chlorine or fluorine, $R^4$ represents hydrogen or methyl, $R^5$ represents hydrogen, $R^6$ represents hydrogen, m represents 0 or 1, n represents 0 or 1, R' represents hydrogen, straight-chain or branched alkyl having 1 to 6 carbon atoms or phenyl, which can optionally be substituted by 1 to 5 identical or different substituents from the group comprising methyl, methoxy, ethoxy, hydroxyl, nitro, fluorine, chlorine, carboxyl, $C_1$–$C_3$-alkoxycarbonyl and cyano, and R" represents hydrogen, straight-chain or branched alkyl having 1 to 4 carbon atoms or phenyl, wherein R' and R", together with the carbon atom to which they are bonded, can also form a 5- or 6-membered aliphatic ring.

Compounds which are particularly preferred for the process according to the invention are those of the formula (II)

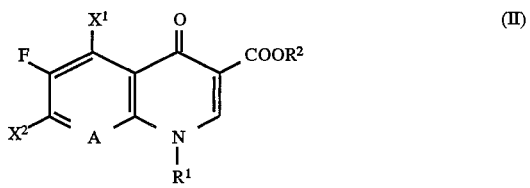

in which $X^1$ represents hydrogen, amino, methoxy, fluorine, chlorine or methyl, $X^2$ represents fluorine or chlorine, $R^1$ represents methyl, ethyl, tert.-butyl, vinyl, cyclopropyl, 2-fluoroethyl, 4-fluorophenyl or 2,4-difluorophenyl, $R^2$ represents hydrogen, methyl or ethyl and A represents N or C—$R^7$, wherein $R^7$ represents hydrogen, fluorine, chlorine, methyl or methoxy, or together with $R^1$ can also form a bridge having the structure

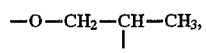

and those of the formula (III)

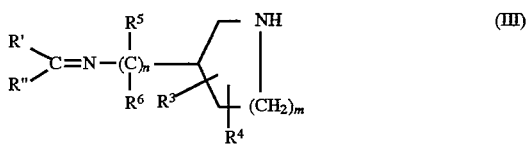

in which $R^3$ represents hydrogen, methyl, hydroxyl, methoxy, methylthio, ethylthio or fluorine, $R^4$ represents hydrogen or methyl, $R^5$ represents hydrogen, $R^6$ represents hydrogen, m represents 0 or 1, n represents 0 or 1, R' represents hydrogen, straight-chain or branched alkyl having 1 to 5 carbon atoms or phenyl, which can optionally be substituted by 1 to 4 identical or different substituents from the group comprising methyl, methoxy, hydroxyl, nitro, fluorine, chlorine, carboxyl and $C_1$–$C_2$-alkoxycarbonyl, and R" represents hydrogen, straight-chain or branched alkyl having 1 to 3 carbon atoms or phenyl, wherein R' and R", together with the carbon atom to which they are bonded, can also form a 5- or 6-membered aliphatic ring.

The invention likewise relates to compounds of the formulae (III) and (IV), although compounds of the formula (IV) in which, simultaneously, R" represents H, n represents 0, m represents 1, $R^3$ and $R^4$ represent H, $X^1$ represents H, A represents CH, $R^2$ represents H or a carboxyl-protective group, $R^1$ represents $C_1$–$C_5$-alkyl, cyclopropyl or phenyl which is optionally substituted by 1 or 2 fluorine atoms and R' represents phenyl or substituted phenyl are excluded.

The compounds of the formula (II) used as starting substances are known or can be prepared by known methods. Examples which may be mentioned are:

7-chloro-1-cyclopropyl-6-fluoro-1,4-dihydro-4-oxo-3-quinolinecarboxylic acid (U.S. application Ser. No. 436,112 filed Oct. 22, 1982, now abandoned, corresponding to German Application 3,142,854) 1-cyclopropyl-6,7-difluoro-1,4-dihydro-4-oxo-3-quinolinecarboxylic acid (European Patent Application 113,091), 8-chloro-1-cyclopropyl-6,7-difluoro-1,4-dihydro-4-oxo-3-quinolinecarboxylic acid (U.S. application Ser. No. 735,500 filed, May 17, 1985, now pending, corresponding to German Application 3,420,743) 1-cyclopropyl-6,7,8-trifluoro-1,4-dihydro-4-oxo-3-quinolinecarboxylic acid (U.S. Pat. No. 4,556,658)

1-cyclopropyl-6,7-difluoro-1,4-dihydro-8-methyl-4-oxo-3-quinolinecarboxylic acid, 6,7-difluoro-1-ethyl-1,4-dihydro-4-oxo-3-quinolinecarboxylic acid, 7-chloro-6-fluoro-1-ethyl-1,4-dihydro-4-oxo-3-quinolinecarboxylic acid, 7-chloro-6-fluoro-1,4-dihydro-1-(2-hydroxyethyl)-4-oxo-3-quinolinecarboxylic acid, 1-cyclopropyl-7-chloro-6-fluoro-1,4-dihydro-8-nitro-4-oxo-3-quinolinecarboxylic acid, 6,7-difluoro-1-(2-fluoroethyl)-1,4-dihydro-4-oxo-3-quinolinecarboxylic acid, 6,7-difluoro-1,4-dihydro-1-methoxy-4-oxo-3-quinolinecarboxylic acid, 6,7-difluoro-1,4-dihydro-1-methylamino-4-oxo-3-quinolinecarboxylic acid, 6,7-difluoro-1,4-dihydro-4-oxo-1-phenyl-3-quinolinecarboxylic acid, 6,7-difluoro-1-(4-fluorophenyl)-1,4-dihydro-4-oxo-3-quinolinecarboxylic acid, 6,7-difluoro-1-(3,4-difluoro-phenyl)-1,4-dihydro-4-oxo-3-quinolinecarboxylic acid, 7-chloro-1-cyclopropyl-6-fluoro-1,4-dihydro-4-oxo-1,8-naphthyridine-3-carboxylic acid, ethyl 1-cyclopropyl-6,7,8-trifluoro-1,4-dihydro-4-oxo-3-quinolinecarboxylate (U.S. Pat. No. 4,556,658)

9,10-difluoro-2,3-dihydro-3-methyl-7-oxo-7H-pyrido-[1,2,3-de][1,4]benzoxazine-6-carboxylic acid (European Patent Application 47,005) and the R- or S-form thereof (U.S. Ser. No. 939,582 filed Dec. 9, 1986, now pending, corresponding to German Application 3,543,513) 8,9-difluoro-6,7-dihydro-5-methyl-1-oxo-1H, 5H-benzo[i,j]-quinolizine-2-carboxylic acid, 7-chloro-6-fluoro-1-phenyl-1,4-dihydro-4-oxo-1,8-naphthyridine-3-carboxylic acid (European Patent Application 153,580), 7-chloro-6-fluoro-1-(4-fluorophenyl)-1,4-dihydro-4-oxo-1,8-naphthyridine-3-carboxylic acid (European Patent Application 153,580), 6,7,8-trifluoro-1,4-dihydro-1-methylamino-4-oxo-3-quinolinecarboxylic acid (U.S. Pat. No. 4,666,920) 1-amino-6,7,8-trifluoro-1,4-dihydro-4-oxo-3-quinolinecarboxylic acid (U.S. Pat. No. 4,666,920) 6,7,8-trifluoro-1,4-dihydro-1-dimethylamino-4-oxo-3-quinolinecarboxylic acid (U.S. Pat. No. 4,666,920)

7-chloro-6-fluoro-1,4-dihydro-8-nitro-4-oxo-1-phenyl-3-quinolinecarboxylic acid, 7-chloro-6-fluoro-1-(4-fluorophenyl)-1,4-dihydro-8-nitro-4-oxo-3-quinolinecarboxylic acid, 6,7-difluoro-1-(4-fluorophenyl)-1,4-dihydro-8-methyl-4-oxo-3-quinolinecarboxylic acid, 6-chloro-7-fluoro-1-(4-fluorophenyl)-1,4-dihydro-4-oxo-3-quinolinecarboxylic acid (European Patent Application 131,839), 6-chloro-7-fluoro-1-(2,4-difluorophenyl)-1,4-dihydro-4-oxo-3-quinolinecarboxylic acid (European Patent Application 131,839), 6,7,8-trifluoro-1-(4-fluorophenyl)-1,4-dihydro-4-oxo-3-quinolinecarboxylic acid (European Patent Application 154,780), 6,7,8-trifluoro-1-(2,4-difluorophenyl)-1,4-dihydro-4-oxo-3-quinolinecarboxylic acid (European Patent Application 154,780), 6,7,8-trifluoro-1,4-dihydro-4-oxo-1-phenyl-3-quinolinecarboxylic acid (European Patent Application 154,780), 7-chloro-1-ethyl-6-fluoro-1,4-dihydro-4-oxo-1,8-naphthyridine-3-carboxylic acid, 6,7-difluoro-1,4-dihydro-4-oxo-1-vinyl-3-quinolinecarboxylic acid, 1-tert.-butyl-7-chloro-6-fluoro-1,4-dihydro-4-oxo-1,8-naphthyridine-3-carboxylic acid, 1-tert.-butyl-6,7-difluoro-1,4-dihydro-4-oxo-3-quinolinecarboxylic acid, 1-tert.-butyl-6,7,8-trifluoro-1,4-dihydro-4-oxo-3-quinolinecarboxylic acid, 1-cyclopropyl-6,7-difluoro-1,4-dihydro-5-methyl-4-oxo-3-quinolinecarboxylic acid and ethyl 7-chloro-1-(2,4-difluorophenyl)-6-fluoro-1,4-dihydro-4-oxo-1,8-naphthyridin-3-carboxylate.

The intermediate compounds of the formula (III) are novel. They are prepared by condensation of an oxo compound of the formula (V) with an amino compound of the formula (VI), water being eliminated.

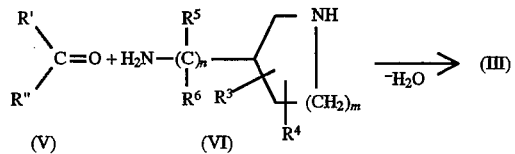

Chiral amino compounds of the formula (VI) can be employed either as racemates or as enantiomerically pure or diastereomerically pure compounds.

The reaction of (V) with (VI) is carried out either without a diluent or in a diluent, such as, for example, acetonitrile, dimethylformamide, dimethylsulphoxide, sulpholane, an alcohol, such as methanol, ethanol, propanol or isopropanol, an ether, such as diethyl ether, diisopropyl ether, glycol monomethyl ether, tert.-butyl methyl ether, dioxane or tetrahydrofuran, an aromatic or aliphatic hydrocarbon, such as toluene, xylene, chlorobenzene, methylene chloride, pentane, hexane or cyclohexane, or pyridine. Mixtures of these diluents can also be used.

The reaction of (V) with (VI) is usually carried out without further additives. However, it is also possible to add catalytic amounts of an inorganic or organic acid, such as sulphuric acid, hydrochloric acid, benzenesulphonic acid, p-toluenesulphonic acid or an acid ion exchanger. Sodium sulphate, magnesium sulphate, calcium chloride or a molecular sieve can be added as a water-binding agent. The reaction can also be carried out in an apparatus which separates off water.

The reaction temperatures can be varied within a substantial range. The reaction is in general carried out between about −20° C. and 120° C., preferably between 0° C. and 50° C.

The reaction can be carried out under normal pressure or under increased pressure. It is in general carried out under pressures between about 1 bar and about 10 bar, preferably under normal pressure.

The compounds of the formula (III) can be isolated from the reaction mixture, for example by fractional distillation.

However, the compounds of the formula (III) can also advantageously be reacted with the compounds of the formula (II) in a one-pot process without intermediate isolation, to give compounds of the formula (I). This in situ preparation is particularly appropriate if the compounds of the formula (III) are difficult to isolate, such as, for example, in the reaction of 3-aminopyrrolidine with aromatic aldehydes. On the other hand, the isolation of the intermediate product of the formula (III) may be advantageous if the amino component (VI) has to be isolated from a reaction mixture. For example, if 3-aminopyrrolidine is prepared by hydrogenolytic debenzylation of 1-benzyl-3-benzylaminopyrrolidine, the crude reaction solution can be reacted with pivalaldehyde without intermediate isolation of the 3-aminopyrrolidine, and the 3-(2,2-dimethylpropylideneamino)-pyrrolidine can be isolated in a simple manner.

The process according to the invention, that is to say the protection of the amino compounds of the formula (VI) by a carbonyl compound of the formula (V) and the subsequent selective reaction of the reaction product (III) with 7-halogenoquinolonecarboxylic acids of the formula (II), is to be regarded as exceptionally surprising inasmuch as it is known from the literature that aldehydes form cyclic or bicyclic animals with open-chain or cyclic diamines [see, for example, DE 2,739,313; J. Amer. Chem. Soc. 95, 3362 (1973); J. Org. Chem. 53 420 (1988); Liebigs Ann. Chem. 1977, 956 and Eur. J. Med. Chem. 17, 235 (1982)]. Aldehydes can therefore be protected with diamines in organometallic reactions [Aust. J. Chem. 26, 1363 (1973) and Tetrahedron 41, 3803 (1985)].

In view of these publications, it had to be expected that, for example, 3-amino-pyrrolidine reacts with aldehydes to give bicyclic aminals:

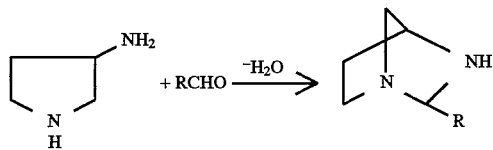

It was therefore to be expected that the bicyclic aminals would react with 7-halogeno-4-quinolone-3-carboxylic acids or -naphthyridone-carboxylic acids of the formula (II) on the secondary rather than on the tertiary nitrogen atom and after elimination of the protective group would lead to 7-(pyrrolidin-3-yl-amino)-quinolone- or -naphthyridone-3-carboxylic acids, so that the specific reaction to give 7-(3-amino-1-pyrrolidinyl)-4-quinolone-3-carboxylic acids or -naphthyridone-carboxylic acids of the formula (I) is surprising.

If, for example, 1-cyclopropyl-6,7,8-trifluoro-1,4-dihydro-4-oxo-3-quinolinecarboxylic acid is reacted with 3-(2,2-dimethylpropylideneamino)-pyrrolidine and the reaction product is treated with hydrochloric acid, 7-(3-amino-1-pyrrolidinyl)-1-cyclopropyl-6,8-difluoro-1,4-dihydro-4-oxo-3-quinolinecarboxylic acid hydrochloride is obtained.

The reaction can be represented by the following equation:

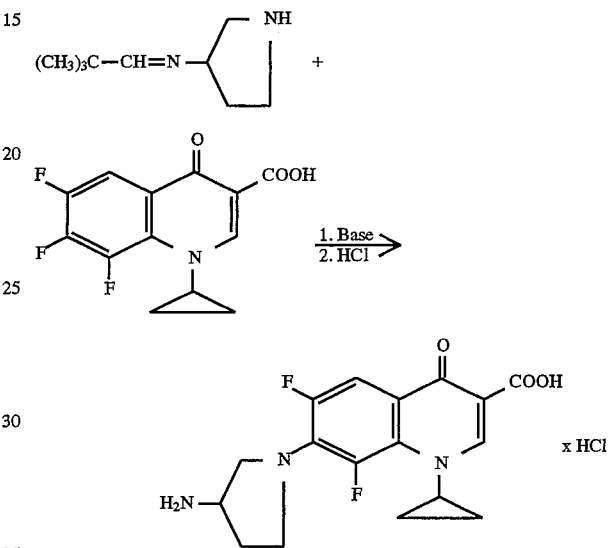

If, for example, the reaction mixture of 3-nitrobenzaldehyde and (S)-3-aminopyrrolidine is reacted with 8-chloro-1-cyclopropyl-6,7-difluoro-1,4-dihydro-4-oxo-3-quinolinecarboxylic acid in a one-pot reaction, the course of the reaction via the intermediately formed 8-chloro-1-cyclopropyl-6-fluoro-1,4-dihydro-7-[(S)-3-(3-nitrobenzylideneamino)-1-pyrrolidinyl]-4-oxo-3-qninolinecarboxylic acid to give 7-[(S)-3-amino-1-pyrrolidinyl]-8-chloro-1-cyclopropyl-6-fluoro-1,4-dihydro-4-oxo-3-quinolinecarboxylic acid hydrochloride can be represented by the following equation:

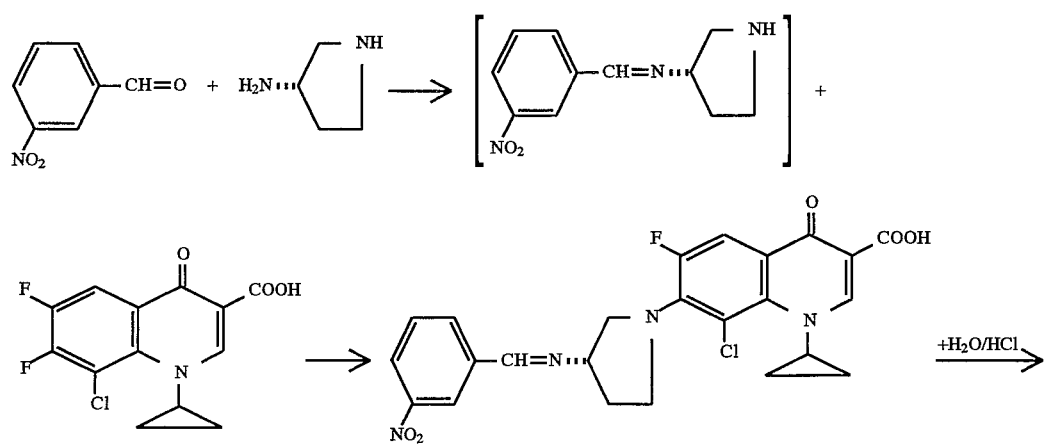

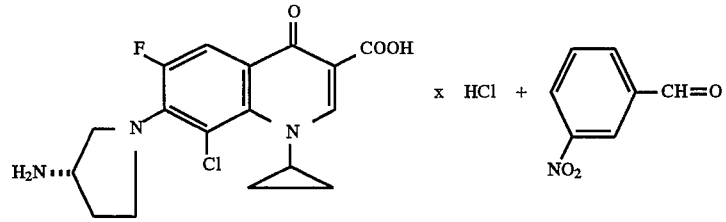

The starting compounds of the formula (V) are known. The following compounds may be mentioned as examples:

Benzaldehyde, 2-chlorobenzaldehyde, 3-chlorobenzaldehyde, 4-chlorobenzaldehyde, 2,4-dichlorobenzaldehyde, 2,6-dichlorobenzaldehyde, 2,4,5-trichlorobenzaldehyde, 2-nitrobenzaldehyde, 3-nitrobenzaldehyde, 4-nitrobenzaldehyde, 4-chloro-3-nitrobenzaldehyde, 2-chloro-5-nitrobenzaldehyde, 2-methylbenzaldehyde, 3-methylbenzaldehyde, 4-methylbenzaldehyde, 3-phenylpropionaldehyde, cinnamaldehyde, 2-, 3- and 4-hydroxybenzaldehyde, 3,5-dichloro-2-hydroxybenzaldehyde, 2-hydroxy-1-naphthaldehyde, 2-hydroxy-3-methoxy-benzaldehyde, 4-hydroxy-3-methoxy-benzaldehyde, 2-, 3- and 4-methoxy-benzaldehde, 2-, 3- and 4-pyridinecarboxaldehyde, 2-fluorobenzaldehyde, 4-fluorobenzaldehyde, 3-fluorobenzaldehyde, 2,4-difluorobenzaldehyde, 3,5-difluorobenzaldehyde, acetaldehyde, propionaldehyde, butyraldehyde, 2-methylbutanal, 2,2-dimethyl-propanal, trichloroacetaldehyde hydrate (chloral hydrate), glyoxal, acetone, butanone, 3-methyl-2-butanone, cyclohexanone and cyclopentanone.

Instead of the oxo compounds (V), it is also possible to use derivatives which behave like oxo compounds under the reaction conditions, such as, for example, acetals or ketals.

The following compounds may be mentioned as examples of starting compounds of the formula (VI), it being possible for chiral compounds to be employed either as racemates or as enantiomerically pure or diastereomerically pure substances:

(R,S)-3-amino-pyrrolidine,
(R)-3-amino-pyrrolidine,
(S)-3-amino-pyrrolidine,
cis- and trans-3-amino-4-methoxy-pyrrolidine,
3-amino-2-methyl-4-methoxy-pyrrolidine,
4-amino-2-methyl-3-methoxy-pyrrolidine,
cis- and trans-3-amino-4-methyl-pyrrolidine,
3-amino-3-methyl-pyrrolidine,
3-amino-2-methyl-pyrrolidine,
4-amino-2-methyl-pyrrolidine,
3-aminomethyl-pyrrolidine,
3-aminomethyl-3-hydroxy-pyrrolidine,
3-aminomethyl-3-methoxy-pyrrolidine,
3-aminomethyl-3-methyl-pyrrolidine,
4-amino-2-hydroxymethyl-pyrrolidine,
3-(1-aminoethyl)-pyrrolidine,
3-amino-azetidine,
3-aminomethyl-azetidine,
3-amino-piperidine,
4-amino-piperidine,
cis- and trans-3-amino-4-methylthio-pyrrolidine and
cis- and trans-3-amino-4-ethylthio-pyrrolidine.

The reaction of (II) with (III) is preferably carried out in a diluent, such as dimethyl sulphoxide, N,N-dimethylformamide, N-methylpyrrolidone, hexamethylphosphoric acid triamide, sulpholane, acetonitrile, water, an alcohol, such as methanol, ethanol, n-propanol or isopropanol, glycol monomethyl ether or pyridine. Mixtures of these diluents can likewise be used, or the diluent can be dispensed with entirely.

Acid-binding agents which can be used are all the customary inorganic and organic acid-binding agents. These include, preferably, the alkali metal hydroxides, alkali metal carbonates, organic amines and amidines. Particularly suitable acid-binding agents which may be mentioned specifically are: triethylamine, 1,4-diazabicyclo[2.2.2]octane (DABCO), 1,8-diazabicyclo[5.4.0]undec-7-ene (DBU) or excess amine (III).

The reaction temperatures can be varied within a substantial range. The reaction is in general carried out between about 20° and 200° C., preferably between 60° C. and 150° C., The reaction can be carried out under normal pressure or under increased pressure. It is in general carried out under pressures between about 1 and 100 bar, preferably between 1 and 10 bar.

In carrying out the process according to the invention, 1 to 5 mols, preferably 1 to 3 mols, of the compound (III) are preferably employed per mol of carboxylic acid (II).

The intermediate compound (IV) formed in the reaction of (II) with (III) does not have to be isolated in pure form. Hydrolyric elimination of the oxo compound (V) from the intermediate compound (IV) often already proceeds during work up in the presence of water at room temperature. It can be accelerated by heating. Under these conditions, the reaction product of the formula (I) is isolated as the betaine.

It is advantageous, after isolation of the intermediate compound (IV), to carry out the elimination of the protective group in the presence of equivalent or excess amounts of an acid, it being possible for the reaction product (I) to be isolated in the form of the salt of this acid. Examples of possible acids are hydrochloric acid, sulphuric acid, acetic acid, trifluoroacetic acid, lactic acid, glycolic acid, succinic acid, citric acid, tartaric acid, methanesulphonic acid, p-toluenesulphonic acid, nicotinic acid, galacturonic acid, gluconic acid, embonic acid, glutmmic acid or aspartic acid.

The eliminated oxo compound (V) can be re-isolated from the reaction batch in a simple manner by extraction with a solvent, such as, for example, methylene chloride, diethyl ether, toluene, ethyl acetate or tert.-butyl methyl ether, and can be fed into the reaction again, which leads to a further simplification and reduction in the costs of the reaction.

The possibility of gentle elimination in a two-phase system of aqueous dilute acid and a water-immiscible extraction agent which dissolves the oxo compound (V) and thus removes it from the reaction solution is of great advantage for quinolonecarboxylic acids containing sensitive radicals.

Thus, for example, 8-chloro-1-cyclopropyl-6-fluoro-1,4-dihydro-7-[3-(3-nitrobenzylideneamino)-1-pyrrolidiny]-4-oxo-3-quinolinecarboxylic acid can be smoothly deblocked with 3N hydrochloric acid in the course of 15 minutes without noticeable 8-dechlorination being observed. In contrast, on deblocking of 7-(3-tert.-butoxycarbonylamino-1-pyrrolidinyl)-3-chloro-1-cyclopropyl-6-fluoro-1,4-dihydro-4-oxo-3-quinolinecarboxylic acid with 3N hydrochloric acid under these conditions, elimination of the protective group takes place to the extent of only about 10% even after 30 minutes, the cleavage product already being contaminated by 7-(3-amino-1-pyrrolidinyl)-1-cyclopropyl-6-fluoro-1,4-dihydro-4-oxo-3-quinolinecarboxylic acid (8-deschloro derivative).

In addition to the active compounds listed in the examples, the following compounds, which can be present as racemates or as enantiomerically pure substances in the form of salts (for example as the hydrochloride, sulphate, methanesulphonate, p-toluenesulphonate or acetate) can be prepared by the process according to the invention:

| $R^1$ | $R^3$ | $X^1$ | A | n |
|---|---|---|---|---|
| cyclopropyl | H | H | N | 0 |
| cyclopropyl | H | H | N | 1 |
| cyclopropyl | CH$_3$O | H | N | 0 |
| cyclopropyl | CH$_3$S | H | N | 0 |
| 2,4-difluorophenyl | H | H | N | 0 |
| 2,4-difluorophenyl | CH$_3$O | H | N | 0 |
| 2,4-difluorophenyl | CH$_3$S | H | N | 0 |
| (CH$_3$)$_3$C— | H | H | N | 0 |
| (CH$_3$)$_3$C | CH$_3$O | H | N | 0 |
| (CH$_3$)$_3$C | CH$_3$S | H | N | 0 |
| cyclopropyl | H | NH$_2$ | CF | 0 |
| cyclopropyl | H | CH$_3$ | CF | 0 |

| $R^1$ | $R^3$ | $X^1$ | A | n |
|---|---|---|---|---|
| cyclopropyl | H | CH$_3$ | CH | 0 |
| cyclopropyl | H | NH$_2$ | CF | 1 |
| cyclopropyl | H | NH$_2$ | CH | 0 |
| cyclopropyl | H | CH$_3$ | CF | 1 |
| cyclopropyl | H | F | CF | 0 |
| cyclopropyl | CH$_3$ | H | CH | 0 |
| cyclopropyl | CH$_3$ | H | CF | 0 |
| cyclopropyl | CH$_3$ | H | CCl | 0 |
| cyclopropyl | CH$_3$ | H | N | 0 |

10-(3-amino-1-pyrrolidinyl)-9-fluoro-2,3-dihydro-3-methyl-7-oxo-7H-pyrido[1,2,3-de][1,4]benzoxazine-6-carboxylic acid and 10-(3(S)-amino-1-pyrrolidinyl)-9-fluoro-2,3-dihydro-3(S)-methyl-7-oxo-7H-pyrido[1,2,3-de][1,4]benzoxazine-6-carboxylic acid.

The intermediate compounds of the formula (IV) exhibit a broad spectrum of antibacterial activity against Gram-positive and Gram-negative germs, in particular against Enterobacteriaceae; above all also against those which are resistant towards various antibiotics, such as, for example, penicillins, cephalosporins, aminoglycosides, sulphonamides and tetracyclines, coupled with a low toxicity.

These useful properties make it possible to use them as chemotherapeutic active compounds in medicine and as substances for preserving inorganic and organic materials, in particular all types of organic materials, for example polymers, lubricants, paints, fibers, leather, paper and wood, and foodstuffs and water.

The compounds (IV) according to the invention are active against a very broad spectrum of microorganisms. With the aid of these compounds, Gram-negative and Gram-positive bacteria and bacteria-like microorganisms can be combated and the diseases caused by these pathogens can be prevented, alleviated and/or cured.

The compounds (IV) according to the invention are particularly active against bacteria and bacteria-like microorganisms. They are therefore particularly suitable in human and veterinary medicine for the prophylaxis and chemotherapy of the local and systemic infections caused by these pathogens.

For example, local and/or systemic diseases which are caused by the following pathogens or by mixtures of the following pathogens can be treated and/or prevented: Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoeae*) and Gram-negative rod-shaped bacilli, such as Enterobacteriaceae, for example *Escherichia coli, Haemophilus influenzae*, Citrobacter (*Citrob. freundii* and *Citrob. divernis*), Salmonella and Shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pt. vulgaris*), Providencia, Yersinia and the genus Acinetobacter. The antibacterial spectrum moreover includes the genus Pseudomonas (*Ps. aeruginosa* and *Ps. maltophilia*) and strictly anaerobic bacteria, such as, for example, *Bacteroides fragilis*, representatives of the genus Peptococcus, Petrostreptococcus and the genus Clostridium; and furthermore Mycoplasma (*M. pneumoniae, M. hominis* and *M. urealyticum*) as well as Mycobacteria, for example *Mycobacterium tuberculosis*.

The following examples document the invention:

EXAMPLE A 3-(2,2-Dimethyl-propylidene-amino)-pyrrolidine 1. 34.5 g (0.4 mol) of 3-aminopyrrolidine are initially introduced into 100 ml of toluene, and 34.5 g (0.3 mol) of 75% strength pivalaldehyde (preparation from Riedel-de-Haen) in 100 ml of toluene are added dropwise at 20° C., while cooling in a water bath. The mixture is subsequently stirred at room temperature for 2 hours, the aqueous phase is then separated off in a separating funnel (4.6 ml) and the toluene solution is dried over sodium sulphate for 1 hour. The toluene is separated off on a rotary evaporator and the residue is distilled using a small Vigreux column. 46.2 g of 3-(2,2-dimethylpropylideneamino)-pyrrolidine of boiling point 61° C./10 mbar are obtained with a purity, determined by gas chromatography, of 98%, corresponding to a yield of 74% and a selectivity of 99% (pivalaldehyde).

2. 8.6 g (0.1 mol) of 3-aminopyrrolidine are initially introduced into the reaction vessel and 8.8 g (0.1 mol) of 97% strength pivalaldehyde (preparation from Aldrich) are added dropwise at 20° C. to 30° C., while cooling in a water bath. The mixture is subsequently stirred at room temperature for 1 hour and is then distilled.

Yield: 13.1 g (85% of theory), boiling point: 60°–63° C./10 mbar; content: 99%.

3. 12.1 g (0.1 mol) of 71% strength pivalaldehyde, initially introduced into the reaction vessel and 8.6 g (0.1 mol) of 3-aminopyrrolidine are added dropwise at 20° C. to 30° C., while cooling in a water bath. The mixture is subsequently stirred at room temperature for 1 hour and is then distilled. Yield: 13.5 g (85% of theory), boiling point: 63° C.–65° C./10 to 12 mbar; content: 97%.

EXAMPLES A 4–9

8.6 g (0.1 mol) of 3-aminopyrrolidine are initially introduced into the reaction vessel, if appropriate in 50 ml of solvent, and pivalaldehyde is added dropwise at 20° C. to 30° C., while cooling in a water bath. The mixture is subsequently stirred at room temperature for 1 hour, an aqueous phase is separated off if appropriate, the solvent is removed on a rotary evaporator and the crude product is distilled.

| Example A | Pival- aldehyde [mol] | Solvent | 3-(2,2-Dimethyl-propyl- ideneamino)-pyrrolidine | | Yield or selectivity [%] |
|---|---|---|---|---|---|
| | | | Content [%] | [g] | |
| 4 | 0.1 | THF | 98 | 12.5 | 79 |
| 5 | 0.1 | — | 97 | 13.0 | 82 |
| 6 | 0.09 | — | 94 | 13.9 | 94 |
| 7 | 0.12 | — | 96 | 13.5 | 84 |
| 8 | 0.09 | CH$_3$OH | 95 | 13.1 | 90 |
| 9 | 0.09 | CH$_3$—O—(CH$_3$)$_3$ | 95 | 13.7 | 94 |

10. 36.8 g (0.138 mol) of 1-benzyl-3-benzylamino-pyrrolidine are hydrogenated in 160 ml of methanol over 5 g of 5% strength palladium on active charcoal at 130° C. under a hydrogen pressure of 100 bar for 10 hours. The catalyst is filtered off and 16.6 g (0.138 mol) of 71% strength pivalaldehyde are added to the filtrate, while stirring, after which the temperature rises from 20° C. to 28° C. The mixture is subsequently stirred for 30 minutes, the methanol is removed on a rotary evaporator and the residue is distilled. 12.7 g of 3-(2,2-dimethyl-propylidene-amino)-pyrrolidine of boiling point: 61° C./10 mbar are obtained with a purity, determined by gas chromatography, of 97%, corresponding to a yield of 58% of theory.

EXAMPLE B 3-(3,5-Difluorobenzylidene-amino)-pyrrolidine

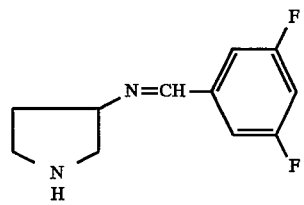

1.72 g (20 mmol) of 3-amino-pyrrolidine are initially introduced into 20 ml of methanol, and 2.84 g (20 mmol) of 3,5-difluorobenzaldehyde are added dropwise at 20° C., while cooling in a water bath. The mixture is subsequently stirred at room temperature for one hour and is concentrated in vacuo on a rotary evaporator, and the residue (4.5 g) is distilled. 0.9 g of an oil, boiling points 80° C.–85° C./0.04 mbar, are obtained, which decomposes to give a highly viscous mass within 4 weeks when stored at room temperature.

EXAMPLE C

3-[(2,2-Dimethylpropylideneamino)-methyl]-pyrrolidine 2.0 g (20 mmol) of 3-aminomethyl-pyrrolidine are initially introduced into 10 ml of methanol, and 1.8 g (22 mmol) of 97% strength pivalaldehyde are added dropwise at room temperature, after which the internal temperature rises to 30° C. The mixture is subsequently stirred for 1 hour and then concentrated, and the residue is distilled through a Vigreux column.

Yield: 2.8 g (80% of theory) of 97% pure product; boiling point: 84°–88° C./11 to 13 mbar.

EXAMPLE D (R)-3-(2,2-Dimethyl-propylideneamino)-pyrrolidine

Analogously to Example A-1, the reaction is carried out with (R)-3-aminopyrrolidine to give (R)-3-(2,2-dimethyl-propylideneamino)-pyrrolidine of boiling point 62° C./8 mbar;

$\alpha_D^{20}=+36.3°$ (c=1.002, CHCl$_3$).

EXAMPLE E (S)-3-(2,2-Dimethyl-propylideneamino)-pyrrolidine

Analogously to Example A-1, the reaction is carried out with (S)-3-aminopyrrolidine to give (S)-3-(2,2-dimethyl-propylideneamino)-pyrrolidine of boiling point 61° C./10 mbar;

$\alpha_D^{20}=-36.5°$ (c=1.0, CHCl$_3$).

EXAMPLE F a) 1-Benzoyl-trans-3-amino-4-methylthio-pyrrolidine 41.5 g (0.24 mol) of 1-benzoyl-2,5-dihydropyrrole are initially introduced into 240 ml of methylene chloride, and 24.8 g (0.3 mol) of methanesulphonyl chloride are added dropwise at 0° C. The mixture is subsequently stirred at room temperature for 16 hours, the solvent is then stripped off under 8 mbar and the residue is taken up in 240 ml of tetrahydrofuran. After addition of 65 g of 25% strength ammonia solution, the mixture is heated at 80° C. in an autoclave for 10 hours. It is then poured into 5 times the amount of water, the pH is brought to 10–11 with sodium carbonate, the mixture is extracted with methylene chloride and the extract is dried over sodium sulphate and concentrated. The crude product (50 g) is chromatographed on silica gel (mobile phase initially ethanol:ethyl acetate 1:3, then ethanol; Rf value: 0.34 ethanol).

Yield: 33.5 g (59% of theory).

b) trans-3-Amino-4-methylthio-pyrrolidine 23.6 g (0.1 mol) of 1-benzoyl-trans-3-amino-4-methylthio-pyrrolidine are stirred with 80 ml of 5N sodium hydroxide solution until a homogeneous solution has formed (2 hours). The solution is then saturated with sodium sulphate and extracted with tert.-butyl methyl ether in a perforator. The extract is dried over sodium sulphate, filtered and concentrated and the residue is distilled.

Yield: 10.5 g (79% of theory), boiling point: 108°–110° C./11 mbar.

c) trans-3-(2,2-Dimethyl-propylideneamino)-4-methylthio-pyrrolidine 1.32 g (10 mmol) of trans-3-amino-4-methylthiopyrrolidine are initially introduced into 5 ml of methanol, and 1.23 ml (11 mmol) of 97% strength pivalaldehyde are added dropwise, after which the temperature rises from 25° to 36° C. The mixture is subsequently stirred for a further 30 minutes, without cooling, the batch is then concentrated and the residue is distilled. Yield: 1.50 g (75% of theory), boiling point: 63° C./0.07 mbar.

EXAMPLE 1

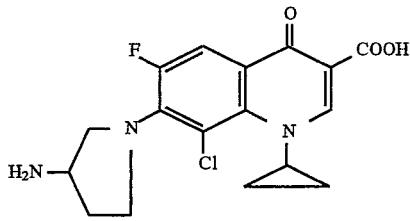

3 g (10 mmol) of 8-chloro-1-cyclopropyl-6,7-difluoro-1,4-dihydro-4-oxo-3-quinolinecarboxylic acid are heated under reflux with 2.2 g (20 mmol) of 1,4-diazabicyclo[2.2.2]octane and 1.7 g (11 mmol) of 3-(2,2-dimethylpropylideneamino)-pyrrolidine in a mixture of 20 ml of acetonitrile and 10 ml of dimethylformamide for 1 hour. The mixture is concentrated in vacuo, the residue is stirred with water and the undissolved residue is filtered off with suction, washed with water and dried at 70° C. in vacuo. The resulting product is recrystallized from a mixture of 35 ml of glycol monomethyl ether and 5 ml of dimethylformamide and washed with ethanol.

Yield: 3.2 g (87.6% of theory) of 7-(3-amino-1-pyrrolidinyl)-8-chloro-1-cyclopropyl-6-fluoro-1,4-dihydro-4-oxo-3-quinolinecarboxylic acid; melting point: 254°–256° C. (with decomposition); content: 100% pure (according to HPLC).

EXAMPLE 2

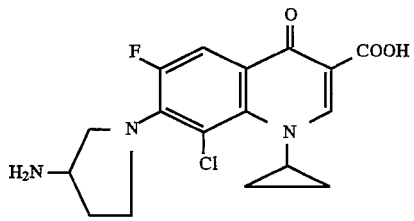

a) A mixture of 0.86 g (10 mmol) of 3-aminopyrrolidine, 1.8 g of molecular sieve (4 Å) and 0.95 g (11 mmol) of pivalaldehyde in 10 ml of acetonitrile is stirred at room temperature for 1 hour, with exclusion of moisture, the solution is decanted off from the molecular sieve and rinsed with 10 ml of acetonitrile, and 10 ml of dimethylformamide are added. 3 g (10 mmol) of 8-chloro-1-cyclopropyl-6,7-difluoro-1,4-dihydro-3-quinolinecarboxylic acid and 2.2 g (20 mmol) of 1,4-diazabicyclo[2.2.2]octane are then added and the mixture is heated under reflux for 1 hour. It is evaporated, the residue is stirred with water (pH 7) and the precipitate is filtered off with suction, washed with water and dried.

Yield: 3.2 g (87.6% of theory) of 7-(3-amino-1-pyrrolidinyl)-8-chloro-1-cyclopropyl-6-fluoro-1,4-dihydro-4-oxo-3-quinolinecarboxylic acid; recrystallization from dimethylformamide gives 2.7 g of the product of melting point 235° C. (with decomposition); content: 98.9% (according to HPLC).

b) 0.95 g (11 mmol) of pivalaldehyde are added dropwise to a solution of 0.86 g (10 mmol) of 3-aminopyrrolidine in 10 ml of acetonitrile at room temperature in the course of 5 minutes, during which the temperature rises from 22.5° C. to 27.5° C. The mixture is subseqently stirred for 1 hour and a virtually complete conversion into 3-(2,2- dimethylpropylideneamino)-pyrrolidine is found by checking the reaction by gas chromatography. The mixture is then diluted with 10 ml of acetonitrile and 10 ml of dimethylformamide, 3 g (10 mmol) of 8-chloro-1-cyclopropyl-6,7-difluoro-1,4-dihydro-3-quinolinecarboxylic acid and 2.2 g (20 mmol) of 1,4-diazabicyclo[2.2.2]octane are added and the mixture is heated under reflux for 1 hour. Work up gives the same result as described under Example 2a).

EXAMPLE 3

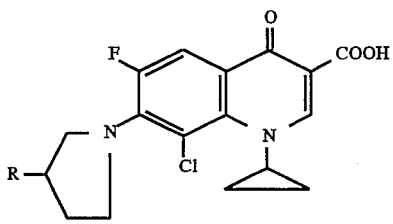

A: R = (CH₃)₃C—CH=N—
B: R = HCl × H₂N—

A) 1.1 g (12.8 mmol) of pivalaldehyde are added to 0.86 g (10 mmol) of 3-aminopyrrolidine at room temperature, during which the temperature rises from 20° C. to 30° C. After 1 hour, the mixture is diluted with 20 ml of acetonitrile and 10 ml of dimethylformamide, 3 g (10 mmol) of 8-chloro-1-cyclopropyl-6,7-difluoro-1,4-dihydro-4-oxo-3-quinolinecarboxylic acid and 2.2 g (20 mmol) of 1,4-diazabicyclo[2.2.2]octane are then added and the mixture is heated under reflux for 1 hour. After cooling, the precipitate is filtered off with suction, washed with acetonitrile and dried at 100° C./12 mbar.

Yield: 3.25 g (75% of theory) of 8-chloro-1-cyclopropyl-7-[3-(2,2-dimethylpropylideneamino)-1-pyrrolidinyl]-6-fluoro-1,4-dihydro-4-oxo-3-quinolinecarboxylic acid of melting point: 181° C. to 182° C.

FAB mass spectrum: m/e 434 (100%, M+H⊕)

$^1$H-NMR spectrum (CF₃COOD): δ 1.45 s (9H), 1.25 m and 1.62 m (4H), 2.65 m and 2.80 m (2H), 4.2 m and 4.4 m (4H), 4.85 m (1H), 5.02 m (1H), 8.22 d (1H), 8.75 s (1H), 9.5 ppm s (1H).

B) 2.3 g (5.3 mmol) of 8-chloro-1-cyclopropyl-7-[3-(2,2-dimethylpropylideneamino)-1-pyrrolidinyl]-6-fluoro-1,4-dihydro-4-oxo-3-quinolinecarboxylic acid are suspended in 15 ml of water at room temperature and dissolved with 10 ml of 1N hydrochloric acid at about 60° C. The solution is filtered, the filtrate is concentrated under a high vacuum and the residue is stirred with ethanol. The precipitate is filtered off with suction and dried in vacuo.

Yield: 1.4 g (65.7% of theory) of 7-(3-amino-1-pyrrolidinyl)-8-chloro-1-cyclopropyl-6-fluoro-1,4-dihydro-4-oxo-3-quinolinecarboxylic acid hydrochloride, melting point: from 280° C. (with decomposition).

EXAMPLE 4

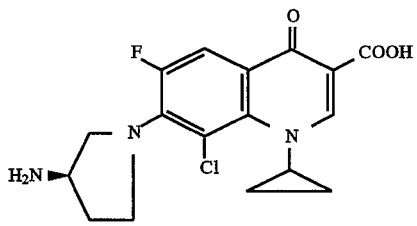

Analogously to Example 1, the reaction is carried out with (R)-3-(2,2-dimethylpropylideneamino)-pyrrolidine to give 7-(R)-3-amino-1-pyrrolidinyl)-8-chloro-1-cyclopropyl-6-fluoro-1,4-dihydro-4-oxo-3-quinolinecarboxylic acid of melting point 252° C.–253° C. (with decomposition) (recrystallized from dimethylformamide).

EXAMPLE 5

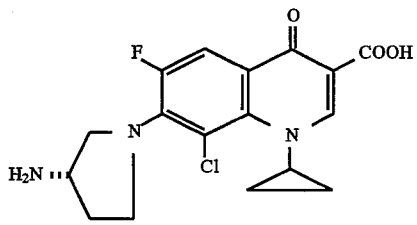

Analogously to Example 1, the reaction is carried out with (S)-3-(2,2-dimethylpropylideneamino)-pyrrolidine to give 7-(S)-3-amino-1-pyrrolidinyl)-8-chloro-1-cyclopropyl-6-fluoro-1,4-dihydro-4-oxo-3-quinolinecarboxylic acid, melting point 253° C.–254° C. (with decomposition).

EXAMPLE 6

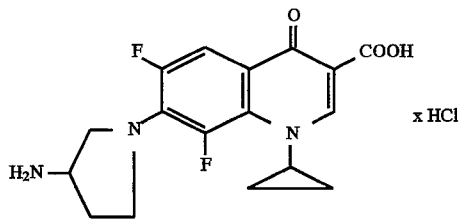

2.8 g (10 mmol) of 1-cyclopropyl-6,7,8-trifluoro-1,4-dihydro-4-oxo-3-quinolinecarboxylic acid are heated under reflux with 2.2 g (20 mmol) of 1,4-diazabicyclo[2.2.2]octane and 1.7 g (11 mmol) of 3-(2,2-dimethylpropylideneamino)-pyrrolidine in a mixture of 20 ml of acetonitrile and 10 ml of dimethylformamide for 1 hour. The mixture is concentrated, the residue is stirred with water, the precipitate is filtered off with suction and then dissolved in 10 ml of half-concentrated hydrochloric acid, the solution is filtered and the hydrochloride is precipitated with ethanol. The crystals are filtered off with suction, washed with ethanol and dried at 80°/12 mbar.

Yield: 2.8 g (72.6% of theory) of 7-(3-amino-1-pyrrolidinyl)-1-cyclopropyl-6,8-difluoro-1,4-dihydro-4-oxo-3-quinolinecarboxylic acid hydrochloride; melting point: 305° C.–306° C. (with decomposition).

If the reaction is carried out analogously with 3-(3,5-difluorobenzylideneamino)-pyrrolidine, the same product is obtained in a 75% yield.

EXAMPLE 7

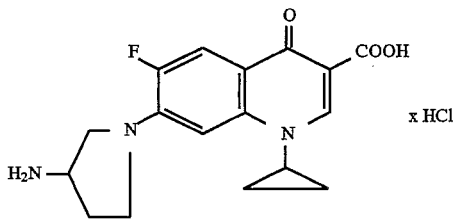

x HCl

Analogously to Example 6, the reaction is carried out with 1-cyclopropyl-6,7-difluoro-1,4-dihydro-4-oxo-3-quinolinecarboxylic acid to give 7-(3-amino-1-pyrrolidinyl)-1-cyclopropyl-6-fluoro-1,4-dihydro-3-quinolinecarboxylic acid hydrochloride of melting point 301° C.–302° C. (with decomposition) in a yield of 93.6% of theory.

EXAMPLE 8

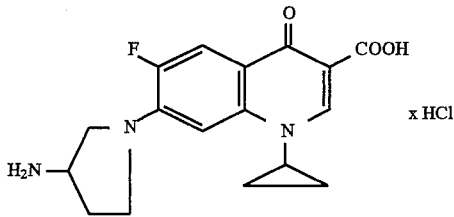

x HCl 1.34 g (11 mmol) of salicylaldehyde are added to 0.86 g (10 mmol) of 3-aminopyrrolidine, the mixture is stirred at room temperature for about 10 minutes and the viscous reaction product is dissolved in a mixture of 20 ml of acetonitrile and 10 ml of dimethylformamide. After addition of 2.2 g (20 mmol), of 1,4-diazabicyclo[2.2.2]octane and 2.65 g (10 mmol) of 1-cyclopropyl-6,7-difluoro-1,4-dihydro-4-oxo-3-quinolinecarboxylic acid, the mixture is heated under reflux for 1 hour and cooled, and the reaction product which has crystallized out is filtered off with suction, washed with acetonitrile and dissolved in 30 ml of half-concentrated hydrochloric acid. The solution is concentrated, the residue is stirred with acetonitrile, the undissolved material is dissolved in 30 ml of water under the influence of heat, the solution is filtered and 100 ml of ethanol are added to the filtrate. The hydrochloride which has precipitated is filtered off with suction, washed with ethanol and dried.

Yield: 2.6 g (70.7% of theory) of 7-(3-amino-1-pyrrolidinyl)-1-cyclopropyl-6-fluoro-1,4-dihydro-3-quinolinecarboxylic acid hydrochloride; melting point: 310° C.–317° C. (with decomposition).

The reaction proceeds in an analogous manner if benzaldehyde, 2-chlorobenzaldehyde, 3-chlorobenzaldehyde, 2,4-dichlorobenzaldehyde, 2-methylbenzaldehyde, 4-methylbenzaldehyde, 4-chlorobenzaldehyde, 4-fluorobenzaldehyde or 3,4-difluorobenzaldehyde is used instead of the salicylaldehyde.

EXAMPLE 9

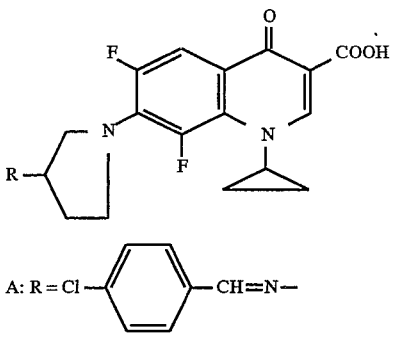

B: R = HCl × H₂N—

A) A mixture of 0.43 g (5 mmol) of 3-aminopyrrolidine and 0.79 g (5.5 mmol) of 97% strength 4-chlorobenzaldehyde is stirred without a solvent for 1 hour. It is then diluted with 10 ml of acetonitrile and 5 ml of dimethylformamide, 1.43 g (5 mmol) of 1-cyclopropyl-6,7,8-trifluoro-1,4-dihydro-4-oxo-3-quinolinecaboxylic acid and 1.1 g of 1,4-diazabicyclo[2.2.2]octane are added and the mixture is heated under reflux for 1 hour. It is cooled and the precipitate which has separated out is filtered off with suction, washed with acetonitrile and dried at 60° C. in vacuo.

Yield: 2.22 g (94.2% of theory) of 7-[3-(4-chlorobenzylideneamino)-1-pyrrolidinyl]-cyclopropyl-6,8-difluoro-1,4-dihydro-4-oxo-3-quinolinecarboxylic acid; melting point: 232° C.–237° C.

¹H-NMR (CF₃COOD): δ 7.75 d and 8.08 d (4H), 8.12 d (1H), 9.07 s (1H), 9.3 ppm s (1H)

B) 2.0 g (4.2 mmol) of the product from stage A are dissolved in 35 ml of hot half-concentrated hydrochloric acid, the solution is filtered hot and after cooling, the hydrochloride is filtered off with suction, washed with ethanol and dried.

Yield: 1.34 g (82% of theory) of 7-(3-amino-1-pyrrolidinyl)-1-cyclopropyl-6,8-difluoro-1,4-dihydro-3-quinolinecarboxylic acid hydrochloride; melting point: 302° C.–305° C. (decomposition).

EXAMPLE 10

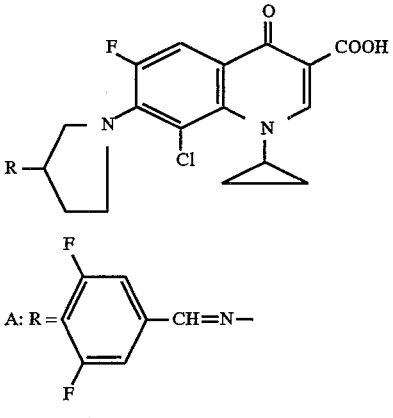

B: R = HCl × H₂N—

A) Analogously to Example 9A), the reaction is carried out with 3,5-difluorobenzaldehyde and 1-cyclopropyl-6,8- difluoro-7-[3-(3,5-difluorobenzylideneamino)-1-pyrrolidinyl]-1,4-dihydro-4-oxo-3-quinolinecarboxylic acid of melting point 225° C.–227° C. (with decomposition) is isolated; mass spectrum: m/e 473 (M⊕), 429 (M⊕-CO$_2$), 349, 346, 288; content: 93% pure.

B) The cleavage of stage A with half-concentrated hydrochloric acid proceeds analogously to Example 9B) to give 7-(3-amino-1-pyrrolidinyl)-1-cyclopropyl-6,8-difluoro-1,4-dihydro-3-quinolinecarboxylic acid hydrochloride, melting point: 303° C.–306° C. (with decomposition).

EXAMPLE 11

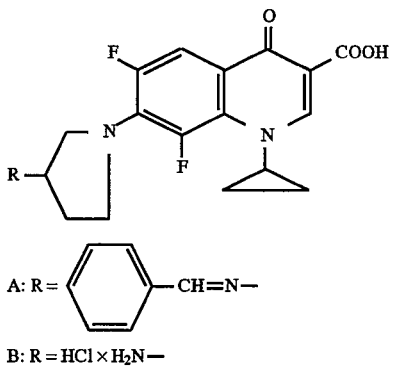

A: R = ⟨phenyl⟩—CH=N—

B: R = HCl × H$_2$N—

A) Analogously to Example 9A), the reaction is carried out with benzaldehyde, followed by isolation of 7-(3-benzylideneamino-1-pyrrolidinyl)-1-cyclopropyl-6,8-difluoro-1,4-dihydro-4-oxo-3-quinolinecarboxylic acid of melting point 207° C.–208° C. (decomposition).

$^1$H-NMR (d$^6$-DMSO): δ 8.6 s (1H), 8.48 s (1H), 7.7 m (3H), 7.45 m (3H), 3.65–4.3 m (6H), 2.25 m and 2.05 m (2H), 1.2 ppm m (4H).

B) The cleavage of stage A) with half-concentrated hydrochloric acid is carried out analogously to Example 9B) to give 7-(3-amino-1-pyrrolidinyl)-1-cyclopropyl-6,8-difluoro-1,4-dihydro-3-quinolinecarboxylic acid hydrochloride; melting point: 300° C.–303° C. (with decomposition).

EXAMPLE 12

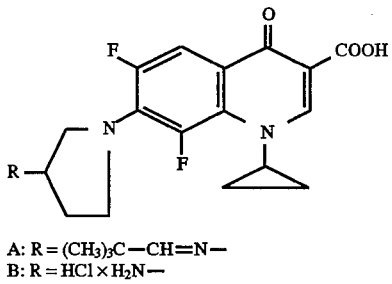

A: R = (CH$_3$)$_3$C—CH=N—
B: R = HCl × H$_2$N—

A) Analogously to Example 9A), the reaction is carried out with pivalaldehyde followed by isolation of 7-[3-(2,2-dimethylpropylideneamino)-1-pyrrolidinyl]-6,8-difluoro-1,4-dihydro-4-oxo-3-quinolinecarboxylic acid of melting point 221° C.–222° C. (with decomposition).

$^1$H-NMR spectrum (CF$_3$COOD): δ 1.46 s (9H), 1.44 m and 1.58 m (4H), 2.63 m and 2.75 m (2H), 4.2–4.55 m (5H), 5.0 m (1H), 8.1 dd (1H), 8.79 s (1H), 9.3 ppm s (1H).

B) The cleavage of stage A) with half-concentrated hydrochloric acid is carried out analogously to Example 9B) to give 7-(3-amino-1-pyrrolidinyl)-1-cyclopropyl-6,8-difluoro-1,4-dihydro-3-quinolinecarboxylic acid hydrochloride; melting point: 305° C.–308° C. (with decomposition).

EXAMPLE 13

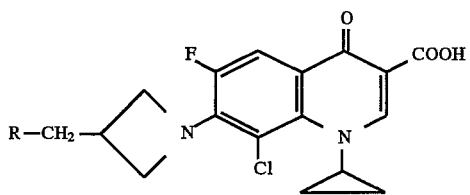

A: R = (CH$_3$)$_3$C—CH=N—
B: R = HCl × H$_2$N—

A) Analogously to Example 9A), the reaction is carried out with pivalaldehyde and 3-aminomethylazetidine, and 1-cyclopropyl-7-[3-(2,2-dimethylpropylidene-aminomethyl)-1-azetidinyl]-6,8-difluoro-1,4-dihydro-4-oxo-3-quinolinecarboxylic acid of melting point 254° C.–256° C. (with decomposition) is obtained.

$^1$H-NMR (d$_6$-DMSO): δ 8.57 s (1H), 7.68 s (1H), 7.65 ppm dd (1H).

B) The cleavage of stage A) with half-concentrated hydrochloric acid analogously to Example 9B) gives 7-(3-aminomethyl-1-azetidinyl)-1-cyclopropyl-6,8-difluoro-1,4-dihydro-3-quinolinecarboxylic acid hydrochloride, which decomposes at about 200° C.

FAB mass spectrum (positive): m/e 386 [(M+HCl+H$^+$)⊕]
FAB mass spectrum (negative): m/e 384 [(M+Cl$^-$)⊖].

EXAMPLE 14

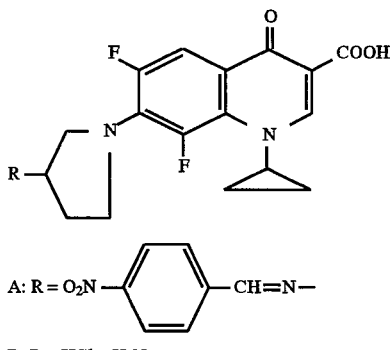

A: R = O$_2$N—⟨phenyl⟩—CH=N—

B: R = HCl × H$_2$N—

A) A solution of 1.66 g (11 mmol) of 4-nitrobenzaldehyde in 10 ml of acetonitrile is added to a solution of 0.86 g (10 mmol) of 3-aminopyrrolidine in 10 ml of acetonitrile and the mixture is stirred at room temperature for 1 hour. It is diluted with 10 ml of dimethylformamide, 2.2 g (20 mmol) of 1,4-diazabicyclo[2.2.2]octane and 2.83 g (10 mmol) of 1-cyclopropyl-6,7,8-trifluoro-1,4-dihydro-4-oxo-3-quinolinecarboxylic acid are added and the mixture is heated under reflux for 1 hour. The suspension is concentrated, the residue is stirred with 60 ml of acetonitrile and the precipitate is filtered off with suction and dried at 80° C. in vacuo.

Yield: 4.5 g (93% of theory) of 1-cyclopropyl-6,8-difluoro-1,4-dihydro-7-[3-(4-nitrobenzylideneamino)-1-pyrrolidinyl]-4-oxo-3-quinolinecarboxylic acid. Melting point: 227° C.–228° C. (with decomposition).

B) 4.3 g (8.9 mmol) of the product from stage A are dissolved in 40 ml of half-concentrated hydrochloric acid, the solution is filtered and concentrated, the residue is stirred with 30 ml of ethanol and the undissolved precipitate is filtered off with suction, washed with ethanol and dried.

Yield: 3.14 g (91% of theory) of 7-(3-amino-1-pyrrolidinyl)-1-cyclopropyl-6,8-difluoro-1,4-dihydro-4-oxo-3-quinolinecarboxylic acid hydrochloride; melting point: 292° C.–294° C. (with decomposition).

EXAMPLES 15 TO 19

Analogously to Example 14A), the following are obtained with:

15A) 2-Nitrobenzaldehyde: 1-cyclopropyl-6,8-difluoro-1,4-dihydro-7-[3-(2-nitrobenzylideneamino)-1-pyrrolidinyl]-4-oxo-3-quinolinecarboxylic acid, melting point: 227° C.–228° C. (with decomposition).

16A) 3-Nitrobenzaldehyde: 1-cyclopropyl-6,8-difluoro-1,4-dihydro-7-[3-(3-nitrobenzylideneamino)-1-pyrrolidinyl]-4-oxo-3-quinolinecarboxylic acid, melting point: 264° C.–266° C. (with decomposition).

17A) 2,4-Dichlorobenzaldehyde: 1-cyclopropyl-7-[3-(2,4-dichlorobenzylideneamino)-1-pyrrolidinyl]-6,8-difluoro-1,4-dihydro-4-oxo-3-quinolinecarboxylic acid, melting point: 209° C.–213° C. (with decomposition).

18A) 4-Methylbenzaldehyde: 1-cyclopropyl-6,8-difluoro-1,4-dihydro-7-[3-(4-methylbenzylideneamino)-1-pyrrolidinyl]-4-oxo-3-quinolinecarboxylic acid, 19A) 4-Methoxybenzaldehyde: 1-cyclopropyl-6,8-difluoro-1,4-dihydro-7-[3-(4-methoxybenzylideneamino)-1-pyrrolidinyl]-4-oxo-3-quinolinecarboxylic acid.

The compounds of Examples 15A) to 19A) can be reacted analogously to Example 14B) to give 7-(3-amino-1-pyrrolidinyl)-1-cyclopropyl-6,8-difluoro-1,4-dihydro-4-oxo-3-quinolinecarboxylic acid hydrochloride.

EXAMPLE 20

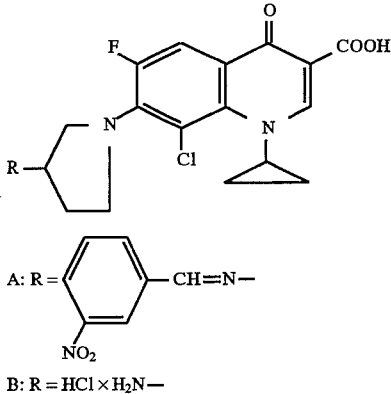

A: R = ⟨phenyl⟩—CH=N—, NO₂
B: R = HCl × H₂N—

A) A solution of 66.4 g (0.44 mol) of 3-nitrobenzaldehyde in 400 ml of acetonitrile is added to a solution of 34.4 g (0.4 mol) of 3-aminopyrrolidine in 400 ml of acetonitrile and the mixture is stirred at room temperature for 1 hour. It is then diluted with 400 ml of dimethylformamide, 88 g (0.79 mol) of 1,4-diazabicyclo[2.2.2]octane and 120 g (0.4 mol) of 8-chloro-1-cyclopropyl-6,7-difluoro-1,4-dihydro-4-oxo-3-quinolinecarboxylic acid are added and the mixture is heated under reflux (about 91° C. to 92° C.) for 1 hour. The resulting suspension is cooled on an ice bath and the precipitate which has separated out is filtered off with suction, washed with acetonitrile and dried.

Yield: 168.5 g (84.5% of theory) of 8-chloro-1-cyclopropyl-6-fluoro-1,4-dihydro-7-[3-(3-nitrobenzylideneamino)-1-pyrrolidinyl]-4-oxo-3-quinolinecarboxylic acid; melting point: 204° C.–207° C. (with decomposition).

B) 120 g (0.24 mol) of the product from stage A) are heated Under gentle reflux (internal temperature 38° C.) in a mixture of 1.8 l of methylene chloride and 2.4 l of 3N hydrochloric acid for 15 minutes. The mixture is cooled on an ice bath and the product which has precipitated out is filtered off with suction, washed thoroughly with acetonitrile and dried in vacuo at 25° C. over KOH.

Yield: 82.7 g (85.5% of theory) of 7-(3-amino-1-pyrrolidinyl)-8-chloro-1-cyclpropyl-6-fluoro-1,4-dihydro-4-oxo-3-quinolinecarboxylic acid hydrochloride; melting point: 279° C.–281° C. (with decomposition) $C_{17}H_{17}ClFN_3O_3 \times HCl$ (402): calculated: C 50.7 H 4.5 N 10.4 Cl 17.7 found: C 50.4 H 4.6 N 10.4 Cl 17.4

The product contains 0.01% of 7-(3-amino-1-pyrrolidinyl)-1-cyclopropyl-6-fluoro-1,4-dihydro-4-oxo-3-quinolinecarboxylic acid hydrochloride (8-deschloro derivative).

The 3-nitrobenzaldehyde can be recovered in a virtuallyquantitative yield by concentrating the methylene chloride phase.

EXAMPLES 21 TO 29

Analogously to Example 20A), the following are obtained with:

21A) 2-Nitrobenzaldehyde: 8-chloro-1-cyclpropyl-6-fluoro-1,4-dihydro-7-[3-(2-nitrobenzylideneamino)-1-pyrrolidinyl]-4-oxo-3-quinolinecarboxylic acid, melting point: 234°–237° C. (with decomposition).

22A) 4-Nitrobenzaldehyde: 8-chloro-1-cyclpropyl-6-fluoro-1,4-dihydro-7-[3-(4-nitrobenzylideneamino)-1-pyrrolidinyl]-4-oxo-3-quinolinecarboxylic acid, melting point: 207°–210° C. (with decomposition).

23A) 2,4-Dichloro-benzaldehyde: 8-chloro-1-cyclpropyl-6-fluoro-1,4-dihydro-7-[3-(2,4-dichlorobenzylideneamino)-1-pyrrolidinyl]-4-oxo-3-quinolinecarboxylic acid, melting point: 198°–202° C. (with decomposition).

24A) 2,6-Dichloro-benzaldehyde: 8-chloro-7-[3-(2,6-dichlorobenzylideneamino)-1-pyrrolidinyl]-1-cyclopropyl-6-fluoro-1,4-dihydro-4-oxo-3-quinolinecarboxylic acid, 25A) 4-Chloro-3-nitro-benzaldehyde: 8-chloro-7-[3-(4-chloro-3-nitro-benzylideneamino-1-pyrrolidinyl]-1-cyclopropyl-6-fluoro-1,4-dihydro-4-oxo-3-quinolinecarboxylic acid, 26A) 2-Methylbenzaldehyde: 8-chloro-1-cyclopropenyl-6-fluoro-1,4-dihydro-7-[3-(2-methylbenzylideneamino)-1-pyrrolidinyl]-4-oxo-3-quinolinecarboxylic acid, 27A) 4-Methylbenzaldehyde: 8-chloro-1-cyclopropyl-6-fluoro-1,4-dihydro-7-[3-(4-methylbenzylideneamino)-1-pyrrolidinyl]-4-oxo-3-quinolinecarboxylic acid, 28A) 4-Methoxybenzaldehyde: 8-chloro-1-cyclopropyl-6-fluoro-1,4-dihydro-7-[3-(4-methoxybenzylideneamino)-1-pyrrolidinyl]-4-oxo-3-quinolinecarboxylic acid, 29A) 4-Hydroxybenzaldehyde: 8-chloro-1-cyclopropyl-6-fluoro-1,4-dihydro-7-[3-(4-hydroxybenzylideneamino)-1-pyrrolidinyl]-4-oxo-3-quinolinecarboxylic acid.

The substituted benzylidene protective groups are eliminated under the same conditions as in Example 20B to give 7-(3-amino-1-pyrrolidinyl)-8-chloro-1-cyclopropyl-6-fluoro-1,4-dihydro-4-oxo-3-quinolinecarboxylic hydrochloride.

EXAMPLE 30

A. A solution of 520 mg (3 mmol) of p-toluene-sulphonic acid in 30 ml of water are added to 1 g (2 mmol) of the product from Example 20A in 30 ml of methylene chloride and the mixture is heated under reflux for 15 minutes. After cooling, the product is filtered off with suction, washed with ethanol and dried.

Yield: 0.9 g (84% of theory) of 7-(3-amino-1-pyrrolidinyl)-8-chloro-1-cyclopropyl-6-fluoro-1,4-dihydro-4-oxo-3-quinolinecarboxylic acid p-toluene-sulphonate, melting point 222°–225° C. (with decomposition).

B. 1 g (2 mmol) of the product from Example 20A are heated under reflux in 30 ml of methylene chloride with a solution of 1.8 g of sulphuric acid in 30 ml of water for 1 hour. After cooling, the product is filtered off with suction, washed with ethanol and dried.

Yield: 0.4 g (48% of theory) of 7-(3-amino-1-pyrrolidinyl)-8-chloro-1-cyclopropyl-6-fluoro-1,4-dihydro-4-oxo-3-quinolinecarboxylic acid sulphate, melting point: 210°–215° C. (with decomposition).

EXAMPLE 31

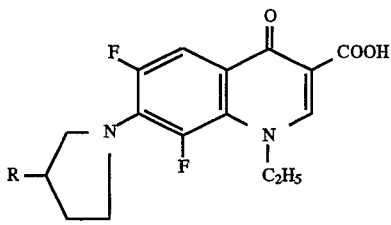

A. R = (CH$_3$)$_3$C—CH=N—
B. R = HCl × H$_2$N—

A. 2.7 g (10 mmol) of 1-ethyl-6,7,8-trifluoro-1,4-dihydro-4-oxo-3-quinolinecarboxylic acid are heated under reflux with 2.2 g (20 mmol) of 1,4-diazabicyclo[2.2.2]octane and 1.7 g (11 mmol) of 3-(2,2-dimethylpropylideneamino)-pyrrolidine in a mixture of 40 ml of acetonitrile and 20 ml of dimethylformamide for 1 hour. After cooling, the precipitate which has separated out is filtered off with suction, washed with acetonitrile and dried.

Yield: 3.57 g (88% of theory) of 7-[3-(2,2-dimethylpropylidene-amino)-1-pyrrolidinyl]-1-ethyl-6,8-difluoro-1,4-dihydro-4-oxo-3-quinolinecarboxylic acid, melting point: 250°–252° C. (with decomposition).

B. 3.5 g (8.6 mmol) of the product from stage A is introduced into a mixture of 40 ml of 4N hydrochloric acid and 30 ml of methylene chloride and the mixture is heated under reflux for 15 minutes. After cooling, the product is filtered off with suction, washed with ethanol and dried.

Yield: 2.8 g (87% of theory) of 7-(3-amino-1-pyrrolidinyl)-1-ethyl-6,8-difluoro-1,4-dihydro-4-oxo-3-quinolinecarboxylic acid hydrochloride, melting point: 288°–290° C. (with decomposition).

EXAMPLE 32

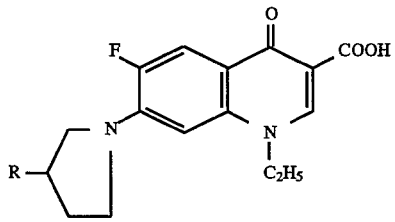

A. R = (CH$_3$)$_3$C—CH=N—
B. R = HCl × H$_2$N—

Analogously to Example 31, the following are obtained with 1-ethyl-6,7-difluoro-1,4-dihydro-4-oxo-3-quinolonecarboxylic acid;

A. 7-[3-(2,2-Dimethylpropylideneamino)-1-pyrrolidinyl]-1-ethyl-6-fluoro-1,4-dihydro-4-oxo-3-quinolinecarboxylic acid, melting point: 262°–268° C. (with decomposition):

B. 7-(3-Amino-1-pyrrolidinyl)-1-ethyl-6-fluoro-1,4-dihydro-4-oxo-3-quinolinecarboxylic acid hydrochloride, melting point: 290°–292° C. (with decomposition).

EXAMPLE 33

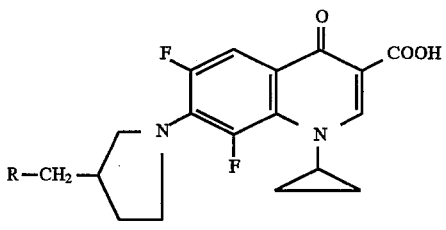

A. R = (CH$_3$)$_3$C—CN=N—

B. R = 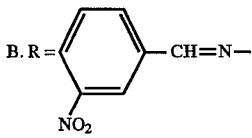—CH=N—

C. R = HCl × H$_2$N—

A. 1.42 g (5mmol) of 1-cyclopropyl-6,7,8-trifluoro-1,4-dichloro-4-oxo-3-quinolinecarboxylic acid are heated under reflux with 1.1 g (10 mmol) of 1,4-diazabicyclo[2.2.2]octane and 920 mg (5.5 mmol) of 3-[(2,2-dimethylpropylideneamino)-methyl]-pyrrolidine in 20 ml of acetonitrile and 10 ml of dimethylformamide for 1 hour. The precipitate which has separated out is filtered off with suction, washed with acetonitrile and dried.

Yield: 1.87 g (87% of theory) of 1-cyclopropyl-7-[3-(2,2-dimethylpropylideneamino-methyl)-1-pyrrolidinyl]-6,8-difluoro-1,4-dihydro-4-oxo-3-quinolinecarboxylic acid, melting point 204°–206° C. (with decomposition).

B. A solution of 1.66 g (11 mmol) of 3-nitrobenzaldehyde in 10 ml of acetonitrile is added to a solution of 1.0 g (10 mmol) of 3-aminomethyl-pyrrolidine in 10 ml of acetonitrile, during which the temperature of the mixture rises from 21° C. to 24° C., and the mixture is subsequently stirred at room temperature for 1 hour. It is then diluted with 10 ml of dimethylformamide, 2.2 g (20 mmol) of 1,4-diazabicyclo[2.2.2]octane and 2.83 g (10 mmol) of 1-cyclopropyl-6,7,8-trifluoro-1,4-dihydro-4-oxo-3-quinolinecarboxylic acid are added and the mixture is heated under reflux for 1 hour. The precipitate is filtered off with suction, washed with acetonitrile and dried.

Yield: 4.7 g (95% of theory) of 1-cyclopropyl-6,8-difluoro-1,4-dihydro-7-[3-(3-nitrobenzylideneaminomethyl)-1-pyrrolidinyl]-4-oxo-3-quinolinecarboxylic acid, melting point: 184°–186° C. (with decomposition).

C. 2.7 g (5.4 mmol) of the product from Example 33B is heated under reflux in a mixture of 40 ml of methylene chloride and 40 ml of 3N hydrochloric acid for 75 minutes. After cooling, the precipitate is filtered off with suction, washed with ethanol and dried.

Yield: 1.35 g (62% of theory) of 7-(3-aminomethyl-1-pyrrolidinyl)-1-cyclopropyl-6,8-difluoro-1,4-dihydro-4-oxo-3-quinolinecarboxylic acid hydrochloride, melting point: 290°–295° C. (with decomposition).

Cleavage of the product from Example 33A with hydrochloric acid gives the same result.

EXAMPLE 34

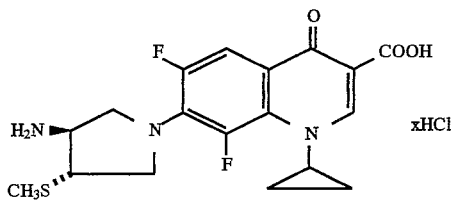

Analogously to Example 33A, the reaction is carried out with trans-3-(2,2-dimethylpropylideneamino)-4-methylthio-pyrrolidine to give 1-cyclopropyl-7-[trans-3-(2,2-dimethylpropylideneamino-4-methylthio)-1-pyrrolidinyl]-6,8-difluoro-1,4-dihydro-4-oxo-3-quinolinecarboxylic acid, and this is cleaved analogously to Example 32C to give 7-(trans-3-amino-4-methylthio-1-pyrrolidinyl)-1-cyclopropyl-6,8-difluoro-1,4-dihydro-4-oxo-3-quinolinecarboxylic acid hydrochloride, melting point: 255°–257° C. (with decomposition).

EXAMPLE 35

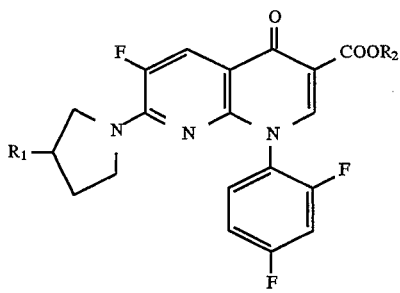

A. R₁ = (CH₃)₃C—CH=N—, R₂ = C₂H₅
B. R₁ = HCl × H₂N—, R₂ = H

A. 1.1 g (12.8 mmol) of pivalaldehyde are added to 0.86 g (10 mmol) of 3-amino-pyrrolidine at room temperature and after 1 hour the mixture is diluted with 20 ml of acetonitrile and 10 ml of dimethylformaldehyde. 1.1 g (10 mmol) of 1,4-diazabicyclo-[2.2.2]octane and 3.8 g (10 mmol) of ethyl 7-chloro-1-(2,4-difluorophenyl)-6-fluoro-1,4-dihydro-4-oxo-1,8-naphthyridine-3-carboxylate are added and the mixture is stirred overnight at room temperature. The precipitate is filtered off with suction, washed with water and dried in vacuo at 100° C.

Yield: 4.25 g (85% of theory) of ethyl 1-(2,4-difluorophenyl)-7-[3-(2,2-dimethyl-propylidene-amino)-1-pyrrolidinyl]-6-fluoro-1,4-dihydro-4-oxo-1,8-naphthyridine-3-carboxylate of melting point: 197°–198° C. (with decomposition).

¹H-NMR (CDCl₃): δ 1.05 s (9H), 1.4 t (3H), 1.9 m und 2.05 m (2H), a broad m at 3.5–3.7 (6H), 4.4 q (2H), 7.05 m (2H), 7.4 m (1H), 8.05 d (1H), 8.35 ppm s (1H).

B. 1.5 g (3 mmol) of the product of step A are heated under reflux in a mixture of 15 ml of acetic acid and 12 ml of half-concentrated hydrochloric acid for 6 hours. The mixture is concentrated in vacuo and the residue is washed with dichloromethane and recrystallized from glycol monomethyl ether.

Yield: 0.9 g (68% of theory) of 7-(3-amino-1-pyrrolidinyl)-1-(2,4-difluorophenyl)-6-fluoro-1,4-dihydro-4-oxo-1,8-naphthyridine-3-carboxylic acid hydrochloride of melting point: 275°–283° C. (with decomposition).

It will be appreciated that the instant specification is set forth by way of illustration and not limitation and that various modifications and changes may be made without departing from the spirit and scope of the present invention.

What is claimed is:

1. A process for the preparation of a compound of the formula

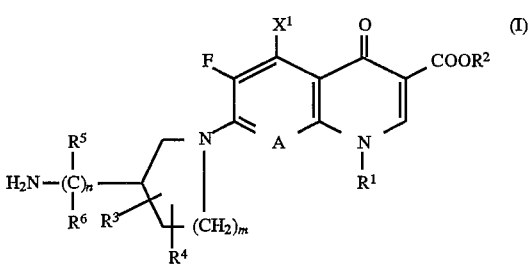

in which $X^1$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or alkyl having 1 to 4 carbon atoms, $R^1$ represents straight-chain or branched alkyl having 1 to 5 carbon atoms, which can optionally be substituted by 1 to 3 halogen atoms, or alkenyl having 2 to 4 carbon atoms, cycloalkyl having 3 to 6 carbon atoms, 2-hydroxyethyl, methoxy, amino, methylamino, ethylamino, dimethylamino or phenyl which is optionally substituted by 1 or 2 fluorine atoms, $R^2$ represents hydrogen, alkyl having 1 to 4 carbon atoms or (5-methyl-2-oxo-1,3-dioxol-4-yl)-methyl, $R^3$ represents hydrogen, $C_1$–$C_3$-alkyl, hydroxyl, $C_1$–$C_3$-alkoxy, $C_1$–$C_3$-alkylthio or halogen, $R^4$ represents hydrogen or methyl, $R^5$ and $R^6$ are identical or different and represent hydrogen or methyl, m represents 0, 1 or 2, n represents 0 or 1 and A represents N or C—$R^7$ wherein
  $R^7$ represents H, halogen, methyl, cyano, nitro, hydroxyl or methoxy, or together with $R^1$ can also form a bridge having the structure

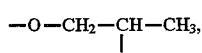

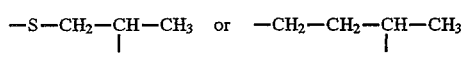

which can have the R- or S-configuration, which comprises condensing an oxo compound of the formula

 (V)

with an amino compound of the formula

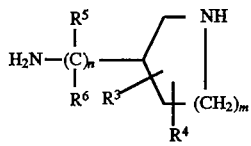 (VI)

in which

R' represents hydrogen, straight-chain or branched alkyl having 1 to 10 carbon atoms or phenyl, which can optionally be substituted by one to five identical or different substituents from the group consisting of $C_1-C_4$-alkyl, $C_1-C_4$-alkoxy, $C_1-C_2$-alkylthio, hydroxyl, nitro, halogen, carboxyl, $C_1-C_4$-alkoxycarbonyl, cyano and phenyl, or represents naphthyl, and R" represents hydrogen, straight-chain or branched alkyl having 1 to 5 carbon atoms or phenyl, wherein R' and R", together with the carbon atom to which they are bonded, can also form a 5- or 6-membered aliphatic ring which is optionally substituted by one or more methyl or ethyl radicals, to produce a compound of the formula

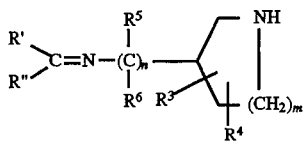 (III)

reacting the compound of the formula (III) with a compound of the formula

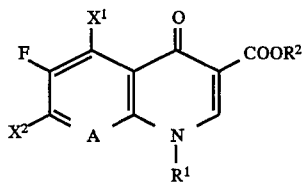 (II)

in which $X^2$ represents halogen, to give a compound of the formula

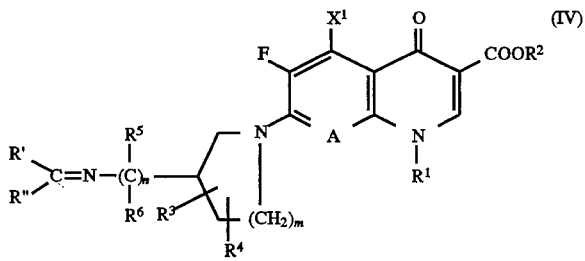 (IV)

and then eliminating the amino-protective group

2. The process according to claim 1, in which $X^1$ represents hydrogen, amino, hydroxyl, alkoxy having 1 or 2 carbon atoms, fluorine, chlorine, bromine or alkyl having 1 to 3 carbon atoms, $X^2$ represents fluorine or chlorine, represents straight-chain or branched alkyl having 1 to 4 carbon atoms, which can optionally be substituted by 1 to 3 fluorine atoms, or alkenyl having 2 to 3 carbon atoms, cycloalkyl having 3 or 4 carbon atoms, 2-hydroxyethyl, 2-fluoroethyl, methylamino, ethylamino, dimethylamino or phenyl which is optionally substituted by 1 or 2 fluorine atoms, $R^2$ represents hydrogen or alkyl having 1 to 3 carbon atoms, A represents N or C—$R^7$, wherein
$R^7$ represents H, fluorine, chlorine, bromine, methyl, hydroxyl or methoxy, or together with $R^1$ can also form a bridge having the structure

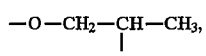

$R^3$ represents hydrogen, methyl, ethyl, hydroxyl, methoxy, ethoxy, methylthio, ethylthio, chlorine or fluorine, $R^4$ represents hydrogen or methyl, $R^5$ represents hydrogen, $R^6$ represents hydrogen, m represents 0 or 1, n represents 0 or 1, R' represents hydrogen, straight-chain or branched alkyl having 1 to 6 carbon atoms or phenyl, which can optionally be substituted by 1 to 5 identical or different substituents from the group consisting of methyl, methoxy, ethoxy, hydroxyl, nitro, fluorine, chlorine, carboxyl, $C_1-C_3$-alkoxycarbonyl and cyano, and R" represents hydrogen, straight-chain or branched alkyl having 1 to 4 carbon atoms or phenyl, wherein R' and R", together with the carbon atom to which they are bonded, can also form a 5- or 6-membered aliphatic ring.

3. The process according to claim 1, in which $X^1$ represents hydrogen, amino, methoxy, fluorine, chlorine or methyl, $X^2$ represents fluorine or chlorine, $R^1$ represents methyl, ethyl, tert.-butyl, vinyl, cyclopropyl, 2-fluoroethyl, 4-fluorophenyl or 2,4-difluorophenyl, $R^2$ represents hydrogen, methyl or ethyl, A represents N or C—$R^7$, wherein
$R^7$ represents hydrogen, fluorine, chlorine, methyl or methoxy, or together with $R^1$ can also form a bridge having the structure

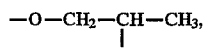

$R^3$ represents hydrogen, methyl, hydroxyl, methoxy, methylthio, ethylthio or fluorine, $R^4$ represents hydrogen or methyl, $R^5$ represents hydrogen, $R^6$ represents hydrogen, m represents 0 or 1, n represents 0 or 1, R' represents hydrogen, straight-chain or branched alkyl having 1 to 5 carbon atoms or phenyl, which can optionally be substituted by 1 to 4 identical or different substituents from the group consisting of methyl, methoxy, hydroxyl, fluorine, chlorine, and $C_1$–$C_2$-alkoxycarbonyl, and R" represents hydrogen, straight-chain or branched alkyl having 1 to 3 carbon atoms or phenyl, wherein R' and R", together with the carbon atom to which they are bonded, can also form a 5- or 6-membered aliphatic ring.

* * * * *

UNITED STATES PATENT AND TRADEMARK OFFICE
CERTIFICATE OF CORRECTION

PATENT NO. : 5,648,493
DATED : July 15, 1997
INVENTOR(S) : Petersen, et al.

It is certified that error appears in the above-indentified patent and that said Letters Patent is hereby corrected as shown below:

Col. 30, line 1   After " chlorine, " insert -- $R^1$ --

Signed and Sealed this

Twenty-fourth Day of March, 1998

Attest:

BRUCE LEHMAN

*Attesting Officer*     *Commissioner of Patents and Trademarks*